United States Patent [19]
Zweymuller et al.

[11] Patent Number: 5,133,770
[45] Date of Patent: Jul. 28, 1992

[54] SHAFT FOR PROSTHESIS

[75] Inventors: Karl Zweymuller, Vienna, Australia; Rudolf Koch, Berlingen, Switzerland

[73] Assignee: Sulzer Brothers Limited, Winterthur, Switzerland

[21] Appl. No.: 603,783

[22] Filed: Oct. 25, 1990

[30] Foreign Application Priority Data

Nov. 16, 1989 [CH] Switzerland ............ 4131/89

[51] Int. Cl.$^5$ .............................................. A61F 2/32
[52] U.S. Cl. ........................................ 623/23; 623/16
[58] Field of Search ....................... 623/23, 18, 21, 20

[56] References Cited

FOREIGN PATENT DOCUMENTS

| | | | |
|---|---|---|---|
| 0131178 | 1/1985 | European Pat. Off. | 623/23 |
| 2839092 | 3/1980 | Fed. Rep. of Germany | 623/23 |
| 3811207 | 10/1989 | Fed. Rep. of Germany | 623/23 |
| 2502939 | 10/1982 | France | 623/23 |
| 2539295 | 7/1984 | France | 623/23 |
| 0471394 | 5/1952 | Italy | 623/23 |

*Primary Examiner*—David Isabella
*Assistant Examiner*—Debra S. Brittingham
*Attorney, Agent, or Firm*—Kenyon & Kenyon

[57] ABSTRACT

A shaft for a hip joint prosthesis is provided with a square cross-section in the distal region of the shaft. In addition, teeth are provided along each corner of the shaft to provide support on a cortical bone. At least some of other teeth are directed in the proximal direction to displace the osseous tissue rather than to exert a cutting force on the osseous tissue. The angular stresses occurring when the shaft is inserted in a bone are reduced without the loss of the spaces between the sides of the shaft and bone for the growth of osseous tissue and a revascularization of the bone.

13 Claims, 2 Drawing Sheets

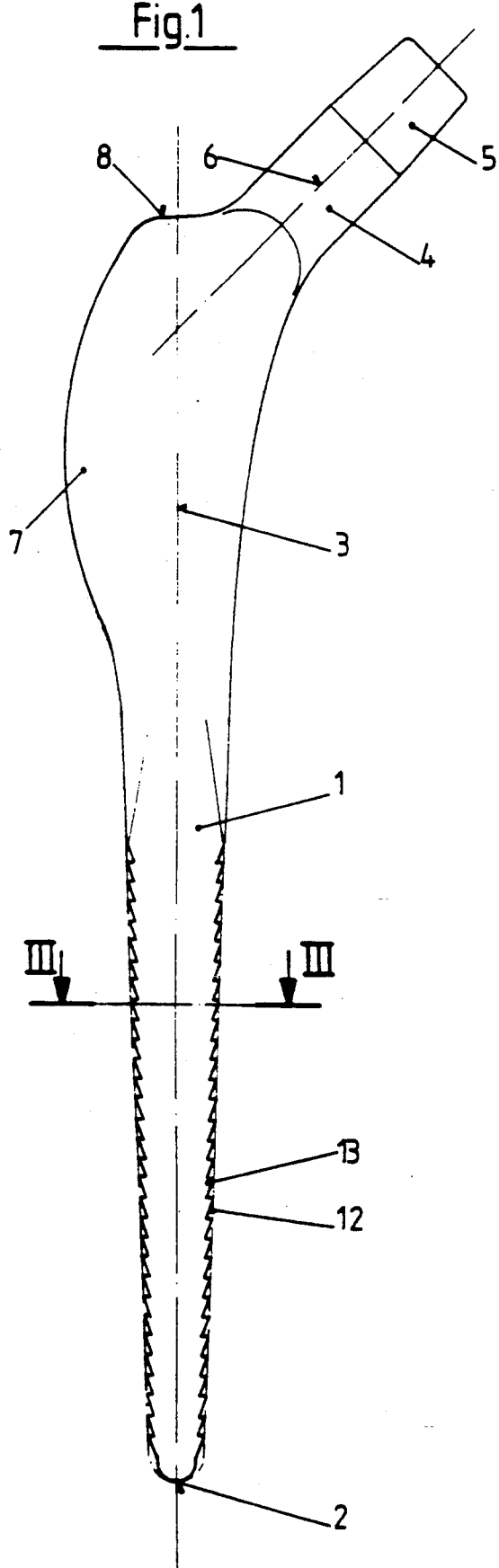
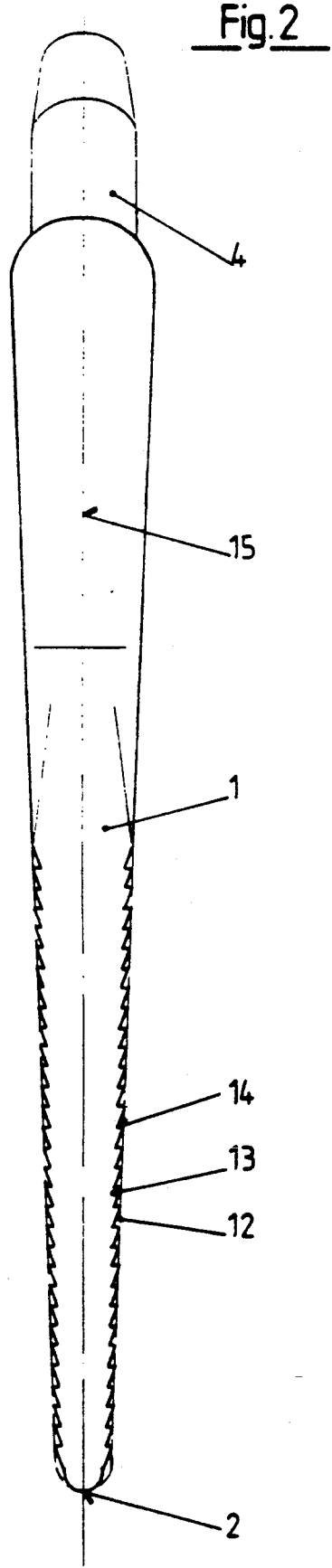

SHAFT FOR PROSTHESIS

This invention relates to a shaft for a prosthesis. Particularly, this invention relates to a straight shaft for a hip joint prosthesis.

Heretofore, various types of shafts have been provided on prostheses for implantation, for example, in a femur bone. In some cases, the shafts have been of smooth surface construction while in other cases, the surfaces of the shafts have been provided with grooves or recesses in order to improve anchorage. For example, French Patent Application 2 539 295 and French Patent Application 2 502 939 describe shafts which have teeth disposed along opposite surfaces as well as recesses on other surfaces.

German OS 2839092 describes a shaft which is made of cruciform shape with teeth-like projections extending along each leg of the shape. German OS 3811207 and European Patent Application 0 131 178 describe shafts which have smooth surfaces along a distal end while having cerated surfaces at a proximal end.

As is known, cavities made by a surgeon in a femur bone in order to receive attachment shafts of femur head prostheses are very frequently constructed so that they are, at least, almost circular, conical bores, at least in the distal region. In practice, it has been shown that shafts having an angular cross-section can be advantageously inserted into such artificially created cavities. In the case of shafts which are primarily supported with their corners on the bone, clearances remain between the surfaces of the shaft and the bone walls to provide spaces into which bone substance may grow. Preferably the shaft surfaces into which bone substance grows are directed laterally and medially, while a revascularisation of the osseous tissue, which improves the nutrition of the living osseous tissue, occurs in these clearances in front of the surfaces pointing in the anterior and posterior direction.

Shaft constructions of the aforementioned type are described in Swiss Patent 642 252. With these known shafts, at least the distal region has a rectangular cross-section. Practice has now shown that when such shafts are driven or pressed into the surrounding cortical osseous tissue, circumferential stresses occur which vary very strongly in the circumferential direction.

Experiences with the known shafts, in which the sides pointing in the anterior and posterior direction are provided with groove-like depressions, have moreover shown that osseous tissue does not easily grow into such depressions, and that the tissue filling these depressions is generally connective tissue which is not very "stable".

Accordingly, it is an object of the invention to achieve the most uniform possible distribution of circumferential stresses in the circumferential direction and simultaneously to construct a shaft surface so that the tissue growing by the prosthesis consists as far as possible of spongy osseous tissue.

It is another object of the invention to improve the anchorage of a straight shaft of a hip joint prosthesis in a femur bone.

It is another object of the invention to improve the revascularisation of bone after implantation of a prosthesis shaft therein.

Briefly, the invention provides a shaft for a prosthesis having a plurality of plane sides defining a square cross-section in a distal region with each side widening in a proximal direction within the distal region coaxially of a longitudinal axis of the shaft. In addition, each pair of sides defines a corner with a plurality of teeth extending longitudinally of the corner with at least some of the teeth being directed in the proximal direction.

Where the prosthesis is a hip joint prosthesis, a neck extends from the shaft at a proximal end on a neck axis co-planar with the longitudinal axis. In addition, the shaft has a median plane extending perpendicularly of a plane containing the two axes. In this case, the teeth located laterally of the median plane are directed in the proximal direction In addition, the teeth located laterally of the median plane are of a greater depth than the teeth located medially of the median plane.

The shape of the shaft is such that spaces are produced between the generally cylindrical bore of an operating cavity in a femur bone and the sides of the shaft. The spaces permit spongy osseous tissue to form therein, while also permitting revascularisation of the bone to occur. In this case, two of the sides of the shaft are advantageously, at least substantially parallel to the plane containing the two axes defined before while the remaining two sides are at right angles to the plane which contains the neck axis and shaft axis. With this arrangement of the shaft sides, the result has been the revascularisation of the osseous tissue in the spaces which are directed in the anterior and posterior direction while new spongiosa is formed in the spaces located in the lateral and medial direction.

The teeth in the corners of the square cross-section of the shaft also guarantee a stable support on the cortical bone. With the arrangement of the teeth similar to saw teeth with their steep tooth surfaces pointing in the proximal direction, the spongiosa remaining in the cavity created in operation is compressed instead of being "lacerated". Furthermore, the steep tooth surfaces pointing in the proximal direction serve to "convert" the stress generally occurring as traction in the lateral direction into a compressive load for the bone. So as to increase the size of the "working surface" for this compressive load, it is advantageous if the tooth depth of the teeth positioned laterally with respect to the median plane is greater than that of the teeth positioned medially thereof.

The manufacture of the shaft is considerably simplified if the teeth are disposed as individual sprockets. The teeth can be produced by machine on a rotating square blank. In this case, the teeth either directly succeed one another or can be separated from one another by spaces in which the square cross-section is retained.

If during implantation of the shaft an increase in the cutting action of the teeth is to be achieved—apart from the already mentioned displacement of the spongiosa—in the medial region of the bone, the steep tooth surfaces of the teeth positioned medially of the median plane are directed in a distal direction.

These and other objects and advantages of the invention will become more apparent from the following detailed description taken in conjunction with the accompanying drawings wherein:

FIG. 1 illustrates a diagramatic view of a hip joint prosthesis constructed in accordance with the invention from the anterior or posterior direction;

FIG. 2 illustrates a side view of the prosthesis of FIG. 1;

Figure 3:
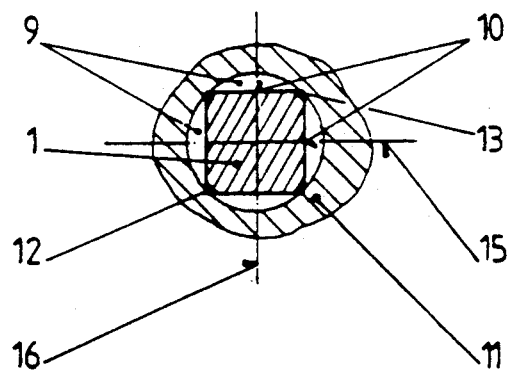
FIG. 3 illustrates a view taken on line III—III of FIG. 1.

Referring to FIGS. 1 and 2, a hip joint prosthesis such as a femur head prosthesis is formed with a shaft 1 having a plurality of plane sides defining a square cross-section (see FIG. 3) in a distal region thereof. Each side of the shaft widens in a proximal direction within the distal region from a distal end to coaxially of a longitudinal axis 3. As indicated, the conical shape of the shaft 1 is symmetrical to the longitudinal central axis 3.

As illustrated in FIG. 1, the shaft 1 changes medially into an arc which continues into a prosthesis neck 4 at a proximal end 8 of the shaft 1. As indicated, a pin or journal 5 is disposed on the neck 4 which tapers conically in the outward direction in order to receive a spherical joint head (not shown). The neck 4 is also disposed on a neck axis 6 which is co-planar with the longitudinal axis 3 of the shaft 1. In addition, the neck axis 6 and shaft axis 3 define an angle which essentially corresponds to the angle between the neck of the femur and the femur axis of a natural hip joint.

As also indicated in FIG. 1, the shaft 1 changes laterally into a flank of a trochanter 7 which extends in an arc to a proximal end 8 of the shaft 1 which is shown horizontally of FIG. 1.

As indicated in FIG. 3, the cross-section of the shaft 1 in the distal region is square with the sides 10 of the square being straight, i.e. having no depressions. This square cross-section extends from the distal end to over approximately one half the shaft height as measured between the two ends 2, 8 and then changes into a rectangular shape which is strongly rounded at the corners or into an oval shape. The square cross-section is orientated with respect to a median plane 15 defined by the shaft axis 3 and neck axis 6 in such a way that two sides 10 of the shaft are at least substantially parallel to the median plane 15 while the remaining two sides are at right angles to the median plane 15. Thus, spaces 9 are formed between the shaft 1 and a cylindrically conical operating cavity produced in the cortical, bone 11. After implantation, spongy osseous tissue is favoritely formed in the spaces 9 before sides 10 of the shaft being at right angles to the median plane and secondly above all a revascularisation of the tissue occurs in spaces 9 before sides 10 pointing in the anterior and posterior directions.

Figure 7:
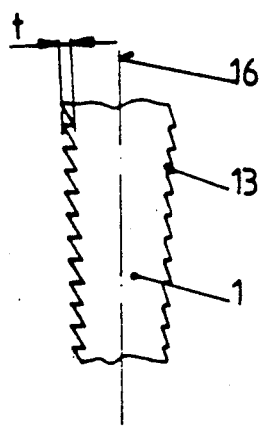
FIG. 7 illustrates a view similar to FIG. 5 showing rows of teeth with different depth.

The shaft 1 has four corners 12 defined by the sides 10 which support the shaft 1 on the cortical bone as indicated in FIG. 3. Further, as indicated in FIGS. 1 and 2, a plurality of teeth 13 extend along each corner 12 of the shaft 1. These teeth are constructed like saw teeth and all of the teeth have steep surfaces 14 which are directed in the proximal direction. In this respect, in order to guarantee a good resistance to tensile strains occurring on the lateral side when loaded, at least the teeth 13 which are positioned laterally with respect to a median plane 16 extending perpendicularly to the pane 15 containing the shaft axis 3 and neck axis 4 are directed with the steep surfaces 14 in the proximal direction. Further, the depth t of these laterally positioned teeth 13 may be greater than that of the teeth which are positioned medially as indicated in FIG. 7.

When the teeth 13 penetrate the osseous tissue, at least the laterally positioned teeth 13 exert a force which displaces the tissue rather than a cutting force.

Figure 5:
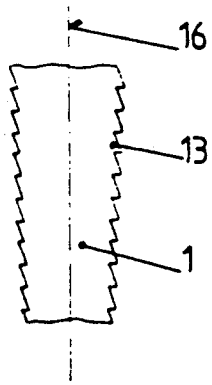
FIG. 5 illustrates a view similar to FIG. 4 of a further embodiment having teeth of opposite corners disposed in opposite directions.

In contrast, in some circumstances, it may be desirable for the teeth 13 to have a cutting action medially. Therefore, it is possible to "rotate" the teeth 13 positioned medially in the second median plane 16 so that the steep surfaces 14 point in the distal direction as indicated in FIGS. 5 and 7.

Figure 4:
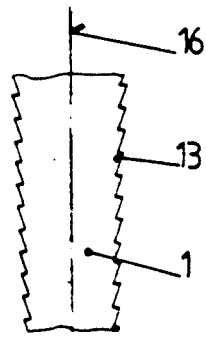
FIG. 4 illustrates a partial view of the shaft of a prosthesis having teeth directed in the proximal direction in accordance with the invention.
Figure 6:
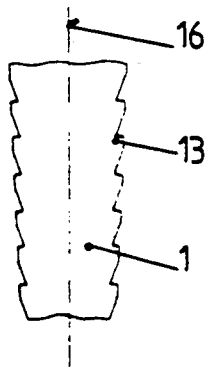
FIG. 6 illustrates an arrangement of teeth being spaced apart along each corner of a shaft in accordance with the invention.

Referring to FIGS. 1 and 2, the teeth 13 are disposed as sprockets and directly follow one another. However, the individual teeth 13 may be disposed in a staggered arrangement as shown in FIG. 4. Still further, the individual teeth 13 can be provided with clearances while the original square cross-section of the shaft 1 is retained as illustrated in FIG. 6.

The invention thus provides a shaft for a prosthesis having a square cross-section with teeth along the corners so as to provide for a secure fixation within a prepared cavity of a bone. In addition, at least the laterally positioned teeth have steep surfaces directed in the proximal direction to avoid cutting of the osseous tissue, above all of the spongy tissue. These teeth serve to displace and comprimer said osseous tissue so that the osseous tissue may form in the spaces between the flat sides of the shaft and the bone while also permitting revascularisation of the bone to occur.

What is claimed is:

1. A prosthesis comprising a shaft having a longitudinal axis, a proximal region with rounded corners, and a plurality of planar sides in a distal region defining a square cross-section, each said side widening in a proximal direction within said distal region coaxially of said longitudinal axis, each pair of sides defining a corner with a plurality of teeth extending longitudinally along said corner, at least some of said teeth having steep tooth surfaces directed in said proximal direction.

2. A as set forth in claim 1 wherein the teeth along two corners on one side of a median plane extending in an anterior-posterior direction have a depth greater than the teeth along the two corners on the opposite side of said plane.

3. A prosthesis as set forth in claim 1 wherein said teeth along at least one corner are directed in a distal direction.

4. A prosthesis as set forth in claim 1 wherein said proximal region is of oval shape in cross-section.

5. A prosthesis as set forth in claim 1 wherein said distal region extends over approximately one-half the shaft height as measured from the ends thereof.

6. A hip joint prosthesis comprising
a shaft having a proximal region with rounded corners, a distal region extending from said proximal region with a plurality of plane sides defining a square cross-section in said distal region thereof, each side widening in a proximal direction within said distal region coaxially of a longitudinal axis; and a plurality of teeth extending along each corner of said shaft between a respective pair of said sides, at least some of said teeth along at least one of said corners being directed in said proximal direction; and
a neck extending from said shaft at a proximal end on a neck axis co-planar with and angularly of said longitudinal axis.

7. A hip joint prosthesis as set forth in claim 6 wherein said shaft has a median plane extending perpendicularly of a plane containing said axes and wherein said teeth located laterally of said median plane are directed in said proximal direction.

8. A hip joint prosthesis as set forth in claim 7 wherein said teeth located laterally of said median plane are of a greater depth than said teeth located medially of said median plane.

9. A hip joint prosthesis as set forth in claim 7 wherein two of said sides of said shaft are at least substantially parallel to and two of said sides are at right angles to said plane containing said axes.

10. A hip joint prosthesis as set forth in claim 7 wherein said teeth positioned medially of said median plane are directed in a distal direction.

11. A hip joint prosthesis as set forth in claim 7 wherein each tooth is of saw tooth shape.

12. A prosthesis comprising a shaft having a longitudinal axis and a plurality of planar sides in a distal region defining a square cross-section, each said side widening in a proximal direction within said distal region coaxially of said longitudinal axis, each pair of sides defining a corner with a plurality of teeth extending longitudinally along said corner, at least some of said teeth being directed in said proximal direction, and said teeth along two corners on one side of a median plane extending in an anterior-posterior direction have a depth greater than the teeth along the two corners on the opposite side of said plane.

13. A hip joint prosthesis comprising
a shaft having a plurality of plane sides defining a square cross-section in a distal region thereof, each side widening in a proximal direction within said distal region coaxially of a longitudinal axis, said shaft having a median plane extending in an anterior-posterior direction; and a plurality of teeth extending along each corner of said shaft between a respective pair of said sides, said teeth extending laterally of said median plane being directed in said proximal direction and being of a greater depth than said teeth located medially of said median plane; and
a neck extending from said shaft at a proximal end on a neck axis co-planar with said longitudinal axis.

* * * * *